Feb. 16, 1960 E. S. BOERNER Plant Pat. 1,905
ROSE PLANT
Filed May 6, 1959
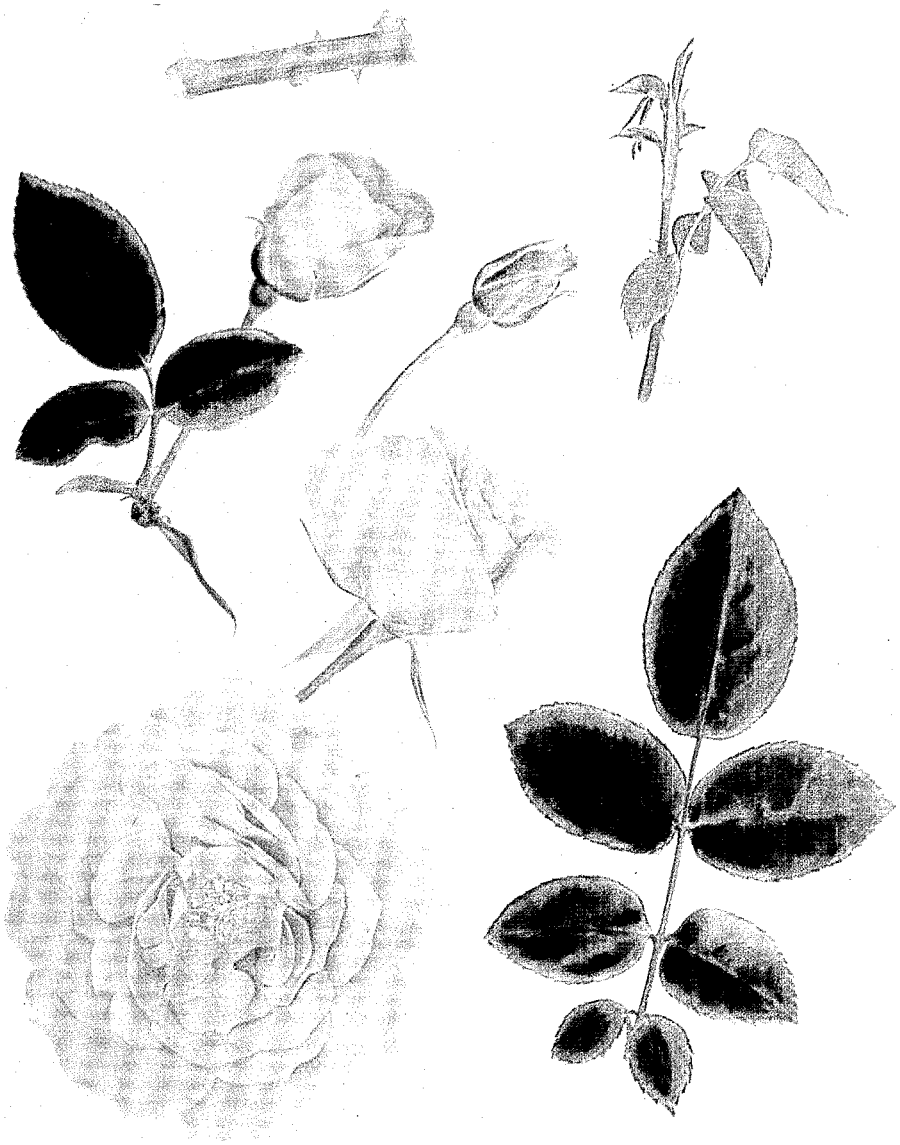
Inventor.
E. S. Boerner
By: Robb & Robb
Attorneys.

United States Patent Office

Plant Pat. 1,905
Patented Feb. 16, 1960

1,905

ROSE PLANT

Eugene S. Boerner, Newark, N.Y., assignor to Jackson & Perkins Company, Newark, N.Y., a corporation of New York Application May 6, 1959, Serial No. 811,510

1 Claim. (Cl. 47—61)

The present invention relates to a new and distinct variety of rose plant of the floribunda class, which was originated by me by crossing an unnamed and unpatented seedling of "World's Fair" (Plant Patent No. 362) with an unnamed and unpatented seedling of "Lavender Pinocchio" (Plant Patent No. 947), said latter seedling parent being characterized by its Lavender colored flowers.

The primary objective of this breeding was to produce a new rose variety of the floribunda class and having Lavender colored flowers. This objective was fully achieved, along with other desirable improvements, as evidenced by the following unique combination of characteristics which are outstanding in the new variety and which distinguish it from its parents, as well as from all other varieties of which I am aware:

(1) Leathery and rugged foliage;

(2) Large and irregular form of the flower head when coming into bloom;

(3) A distinctive Deep Vinaceous-Lavender bud color; and (4) A distinctive and unusually clear Lavender color of the flowers corresponding to Vinaceous-Lavender, lightly overcast with Purplish-Lilac when the flower is fully open.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed Parent.*—An unnamed seedling of "World's Fair."

*Pollen parent.*—An unnamed Lavender colored seedling of "Lavender Pinocchio."

Classification:

*Botanic.*—Floribunda.

*Commercial.*—Floribunda.

*Flower*

(Observations made from specimens grown outdoors at Newark, New York, in the late morning during the early part of June.)

Blooming habit: Recurrent—continuous.

Bud:

*Size.*—Medium.

*Form.*—Ovoid; is not affected by wet or hot weather.

*Color.*—When sepals first divide—Rood's Violet, Plate 11. When petals begin to unfurl—Light Perilla Purple, Plate 37. When half-blown: inside of petals—Deep Vinaceous-Lavender, Plate 44; reverse of petals—Light Vinaceous-Lilac, Plate 44.

*Sepals.*—Smooth edge; curl back when petals begin to unfurl. Color: inside—Light Fluorite Green, Plate 32; outside—Absinthe Green, Plate 31.

*Calyx.*—Color—Light Bice Green, Plate 17. Shape—pear. Size—small. Aspect—smooth, Odor when rubbed—none.

*Peduncle.*—Length—medium. Aspect—rough. Strength—erect; heavy. Color—Grape Green, Plate 41.

*Opening.*—Opens up well; is not affected by adverse weather conditions.

Bloom:

*Size.*—Medium. Average size when fully expanded—from 3½ inches to 4 inches.

*Borne.*—Several together, and in large irregular clusters.

*Stems.*—Medium length; normal strength.

*Form (when first open).*—Open. Permanence—Flattens, and outer petals curl back.

*Petalage.*—Double (full but open center). Number of petals under normal conditions—25.

*Color.*—Center of flower—Purplish-Lilac, Plate 37. Outer petals—Lavender, Plate 36, lightly overcast with Light Pinkish Lilac, Plate 37. Base of petals (aiglet)—Citron Yellow, Plate 16. Inside of petals—Vinaceous Lavender, Plate 44, lightly overcast with Purplish Lilac, Plate 37. Reverse of petals—Lavender, Plate 36. General tonality from a distance—Vinaceous Lavender, Plate 44, lightly overcast with Purplish Lilac, Plate 37.

*Discoloration.*—General tonality at end of first day—Vinaceous Lavender, Plate 44, lightly overcast with Purplish Lilac, Plate 37. Second day—Vinaceous Lavender, Plate 44, lightly overcast with Purplish Lilac, Plate 37. Third day—Lavender, Plate 36, lightly overcast with Purplish Lilac, Plate 37.

Petals:

*Texture.*—Thick; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; small.

*Persistance.*—Drop off cleanly.

*Fragrance.*—Moderate. Nature—fruity (russet apple).

*Lasting quality.*—On the plant—long. As cut flower—long.

*Genital organs*

Stamens, anthers: Medium size; many; regularly arranged around styles. Color—Capucine Orange, Plate 3.

Stamens, filaments (threads): Medium length. Color—Light Salmon-Orange, Plate 2.

Pollen: Color—Pale Yellow-Orange, Plate 3.

Styles: Bunched; even length; medium length; thin.

Stigmas: Color—Capucine Buff, Plate 3.

Ovaries: All enclosed in calyx.

Hips: None.

Seeds: None.

*Plant*

Form: Bush.

Growth: Vigorous; upright.

Foliage: Compound of 3 to 7 leaflets.

*Size.*—Large.

*Quantity.*—Normal.

*Color.*—New foliage: upper side—Deep Dull Yellow-Green (1), Plate 32, with edges Carmine, Plate 1; under side—Carmine, Plate 1, with midrib Courge Green, Plate 17. Old foliage: upper side—Empire Green, Plate 32; under side—Light Cress Green, Plate 31.

*Shape.*—Oval pointed.

*Texture.*—Upper side—leathery; rugged. Under side—smooth.

*Ribs and veins.*—Ordinary.

*Edge.*—Serrated (saw-toothed).

*Serration.*—Single; small.

*Leaf stem.*—Color—Van Dyke Red, Plate 13. Under side—prickly.

*Stipules.*—Medium length; bearded.

Wood:

*New wood.*—Color—Biscay Green, Plate 17. Bark smooth.

*Old wood.*—Color—Light Elm Green, Plate 17. Bark—smooth.

Thorns:

*Thorns.*—Quantity: on main stalks from base—ordinary; on laterals from stalk—ordinary. Form—narrow base; medium length; straight. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of leathery and rugged foliage, large and irregular flower heads when coming into bloom, a distinctive Deep Vinaceous-Lavender bud color, and an unusual clarity of the distinctive Lavender general color tonality of the flowers corresponding to Vinaceous-Lavender lightly overcast with Purplish-Lilac when the flower is fully open.

No references cited.